(12) United States Patent
Didomenico et al.

(10) Patent No.: US 6,307,201 B1
(45) Date of Patent: Oct. 23, 2001

(54) METHOD AND APPARATUS FOR SELECTING A FILTER FOR A REMOTE SENSING DEVICE

(75) Inventors: John D. Didomenico; Craig S. Rendahl, both of Tucson, AZ (US)

(73) Assignee: Envirotest Systems Corp., Sunnyvale, CA (US)

( * ) Notice: Subject to any disclaimer, the term of this patent is extended or adjusted under 35 U.S.C. 154(b) by 0 days.

(21) Appl. No.: 09/223,757

(22) Filed: Dec. 31, 1998

Related U.S. Application Data
(60) Provisional application No. 60/110,195, filed on Nov. 30, 1998.

(51) Int. Cl.$^7$ ............................................ G01N 21/35
(52) U.S. Cl. ................................. 250/339.13; 250/338.5
(58) Field of Search .......................... 250/338.5, 339.13, 250/341.1, 338.12, 339.04, 339.05, 339.06, 339.11, 339.12, 343, 565; 356/437; 702/24, 30; 73/23.31, 23.32

(56) References Cited

U.S. PATENT DOCUMENTS

| | | | |
|---|---|---|---|
| 2,930,893 | 3/1960 | Carpenter et al. | 250/339.13 |
| 3,630,072 | 12/1971 | Traver | 73/23.31 |
| 3,761,724 | 9/1973 | Dennis | 250/565 |
| 3,932,754 * | 1/1976 | Riedl et al. | 250/343 |
| 4,033,169 | 7/1977 | Fujishiro et al. | 73/23.31 |
| 4,323,777 | 4/1982 | Baskins et al. | 250/339.04 |
| 4,412,444 | 11/1983 | Ketel, II | 73/23.32 |
| 4,450,356 | 5/1984 | Murray et al. | 250/339.11 |
| 4,553,032 | 11/1985 | Lo et al. | 250/339.12 |
| 4,707,603 | 11/1987 | Miemelä et al. | 250/339.08 |
| 4,771,176 | 9/1988 | Schiefer et al. | 250/339.13 |
| 4,840,706 * | 6/1989 | Campbell | 162/198 |
| 4,914,719 * | 4/1990 | Conlon et al. | 250/339.13 |
| 4,943,161 | 7/1990 | Michaelis et al. | 356/437 |
| 4,988,446 | 1/1991 | Haberman et al. | 210/656 |
| 4,996,531 | 2/1991 | Bonne et al. | 250/343 |
| 5,157,257 | 10/1992 | Geiger | 250/338.5 |
| 5,210,702 | 5/1993 | Bishop et al. | 702/24 |
| 5,225,679 | 7/1993 | Clarke et al. | 250/343 |
| 5,281,816 | 1/1994 | Jacobson et al. | 250/339.05 |
| 5,281,817 * | 1/1994 | Yelderman et al. | 250/343 |
| 5,319,199 | 6/1994 | Stedman et al. | 250/338.5 |
| 5,343,043 | 8/1994 | Johnson | 250/338.5 |
| 5,348,645 | 9/1994 | Maggard et al. | 208/209 |
| 5,371,367 | 12/1994 | DiDomenico et al. | 250/338.5 |
| 5,390,551 | 2/1995 | Carvajal et al. | 73/863 |
| 5,401,967 | 3/1995 | Stedman et al. | 250/338.5 |
| 5,412,581 | 5/1995 | Tackett | 702/30 |
| 5,489,777 | 2/1996 | Stedman et al. | 250/338.5 |
| 5,498,872 | 3/1996 | Stedman et al. | 250/338.5 |
| 5,591,975 | 1/1997 | Jack et al. | 250/338.5 |
| 5,708,272 | 1/1998 | Ranson et al. | 250/339.12 |
| 5,712,481 | 1/1998 | Welch et al. | 250/339.12 |
| 5,717,209 | 2/1998 | Bigman et al. | 250/339.12 |
| 5,719,396 | 2/1998 | Jack et al. | 250/338.5 |
| 5,726,450 | 3/1998 | Peterson et al. | 250/338.5 |

* cited by examiner

*Primary Examiner*—Seungsook Ham
*Assistant Examiner*—Shun Lee
(74) *Attorney, Agent, or Firm*—Mintz, Levin, Cohn, Ferris, Glovsky and Popeo, P.C.

(57) ABSTRACT

The present invention relates to a system and method for selecting a detection bandwidth centered about a characteristic wavelength of the species to be detected and such that the detection of contaminants is greatly reduced. Contaminants such as pollutants, dust and water are some of the examples of undesirable substances which may be detected by RSD. By selecting the appropriate bandwidth in accordance with this invention, the detection of a desired substance can be separated from the undesirable detection of contaminants.

9 Claims, 4 Drawing Sheets

METHOD AND APPARATUS FOR SELECTING A FILTER FOR A REMOTE SENSING DEVICE

RELATED APPLICATION

Figure 1:
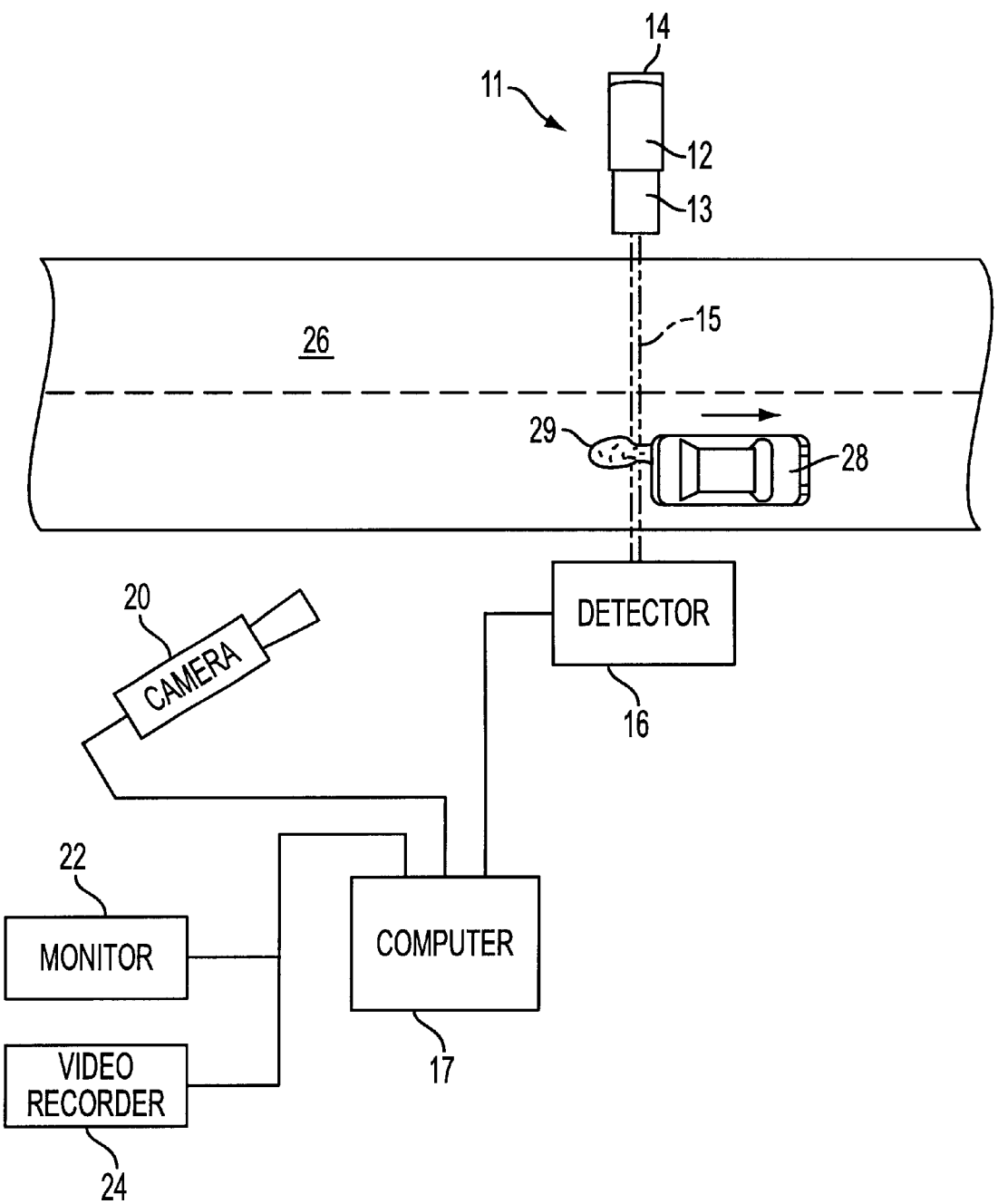

This application claims priority based on U.S. Provisional Patent Application Ser. No. 60/110,195, entitled "Method and Apparatus for Selecting a Filter for a Remote Sensing Device," filed Nov. 30, 1998.

FIELD OF THE INVENTION

This invention relates to a method and apparatus for selecting a filter for a remote sensing device for sensing constituents of a vehicle exhaust emission.

BACKGROUND OF THE INVENTION

In an attempt to improve the quality of the air that we breathe, there has been an increased effort to reduce air pollution due to vehicle emissions. One solution to this growing problem is on-road testing of in-use vehicles using Remote Sensing Devices (RSD). RSD containing infrared and/or ultraviolet radiation detectors are generally known. As vehicles drive by, these RSD measure and record the vehicles' exhaust emissions and other important information.

For example, one known compact, portable RSD comprises an infrared (IR) beam emitter, detectors and a microprocessor. In operation, the RSD measures the concentration of hydrocarbon (HC), carbon monoxide (CO), and carbon dioxide ($CO_2$) within a vehicle's emission. The RSD determines the vehicle's emission concentration by passing a beam of infrared radiation through the vehicle's exhaust as the vehicle travels by the RSD positioned alongside the highway. The IR emitter transmits a beam of IR energy along a path which crosses the traffic lane and encounters a reflector (a mirror) which returns the beam through one or more radiation filters to one or more detectors which are positioned next to the emitter. The IR emitter is located on one side of the vehicle's path (such as a road or highway ramp) at a proper height so that the beam intersects the vehicle's exhaust plume. The IR emitter sends the IR beam into the detectors on a continuous basis. The radiation filters selectively permit radiation of certain characteristic wavelengths to pass through to the detectors while filtering out radiation of other wavelengths. The detectors operate to convert the infrared energy reflected from the reflector(s) to an electrical signal which is measured in voltage and is continuously transferred to the computer where this information is used to compute and produce output signals indicative of the percentage of CO, $CO_2$, and HC in the vehicle's emission.

In order to ensure the accuracy of the exhaust readings, the RSD must be initially calibrated with a gas having known concentrations of CO, $CO_2$, and HC under known atmospheric conditions prior to the vehicle's approach. When there is no vehicle emission in the path, such as during calibration, the detector emits a strong electrical signal because the greater the infrared energy received at the detector, the stronger the electrical signal produced by the detector. However, if there is a presence of CO, $CO_2$, or HC in the infrared light path, these constituents will absorb a portion of the infrared radiation at wavelengths characteristic of each of these emission components. The more CO, $CO_2$, or HC in the exhaust gas; the more radiation at each characteristic wavelength is absorbed, and thus the less radiation sensed by the detectors at these wavelengths. Consequently, the less radiation detected, the lower the level of electrical signal which is generated by the detector. Therefore, the electrical signals emitted by the detectors in response to radiation having the characteristic wavelengths are proportional to the concentration various components of the vehicle's emission.

When a vehicle interrupts the light beam of the RSD, the RSD stores the current readings of the ambient conditions, performs electronic calibration, and starts to monitor the vehicle's emissions. When the exhaust has been sampled, the results are compared to the carbon monoxide, carbon dioxide, hydrocarbon, and nitrogen oxide levels recorded during calibration are stored in the computer memory.

In calculating the concentrations of various components of the vehicle emissions, the computer algorithm relies on detectors coefficients. Emission results are obtained, by computing the ratios of the CO, $CO_2$, and HC voltages to the reference voltages, applying unique detector coefficient, and resealing these arbitrary units into calibrated CO, $CO_2$, and HC values using calibration curves determined in a laboratory utilizing special flow cells with a controlled mixture of CO, $CO_2$, and HC. Those data are then analyzed by the computer by a least squares procedure to determine the amount of each gas constituent within the exhaust emission.

In order for the RSD to accurately determine the concentration of gas, the radiation filters must operate to selectively pass the desired wavelength through to the detector in an efficient and reliable manner. Radiation filters are used to select wavelengths of radiation. A radiation filter works by excluding all but a limited band of radiation centered about a specific wavelength. A radiation filter is a two-port network that passes signals with wavelengths within a specified band (the filter passband) and attenuates signals whose wavelengths lie outside this band (in the filter stopband). The center wavelength is the wavelength that allows the most radiation through the filter within the range of wavelengths that will be passed through.

CO, $CO_2$, and HC each have different characteristic wavelengths because each constituent absorbs infrared energy at different wavelengths. The amount of energy that reaches each detector is critical to the RSD's ability to accurately measure the various gas constituents since the detectors which are employed in the RSD generate an electrical signal proportional to the amount of radiation which impinges on the detector. Thus, it is essential to a system's detection of a vehicle's emission to select radiation filters with the proper center wavelengths and bandwidths to ensure accurate concentration readings.

Existing devices exhibit numerous drawbacks. For example, improper selection of a RSD's radiation filter can generate contamination in the detector's reading which can adversely affect the system's reliability. Contamination occurs when the radiation filter fails to shield out radiation which may be absorbed by other components of the vehicle emission such as water, pollutants, or dust. This radiation may contaminate the reading received at the detector thereby reducing the accuracy of the measurement of the desired constituent within the exhaust emission.

In response to these concerns, RSD have been developed to provide remote emissions testing of vehicles while in use. RSD employ radiation passed through the vehicle exhaust plume to detect and determine the concentration of one or more constituents of the vehicle emission.

These and other drawbacks exist.

SUMMARY OF THE INVENTION

An object of the invention is to overcome these and other drawbacks in existing devices.

Thus, it is an object of the present invention to provide a method of shifting the bandwidth of radiation which impinges on a detector in order to minimize the detection of unwanted contaminants in an RSD system.

It is a further object to select a radiation filter having a proper center wavelength and bandwidth to avoid potential overlap of radiation absorption by both a desirable constituent and undesirable contaminant.

It is still another object to provide a method and apparatus wherein only the component to be detected absorbs radiation within the radiation filter's bandwidth.

Another object is to minimize detection of contaminants by the detector.

The foregoing objects and advantages of the present invention are obtained by shifting the center wavelength and/or adjusting the detection bandwidth of the radiation filter so that the potential for radiation absorption by a contaminant within the detection bandwidth is greatly reduced. In order to achieve this goal, the detection bandwidth of the radiation filter must be selected to have a proper center wavelength and width in order to minimize detection of an undesirable substance. The shift in the radiation filter's center wavelength and/or adjustment of the detection bandwidth permits measurement of substantially only the desirable component and substantially no contaminants. Thus, the effect of contaminants on the electrical signal emitted by the detector is greatly reduced or completely eliminated.

BRIEF DESCRIPTION OF THE DRAWINGS

FIG. 1 illustrates a remote sensing device shown in use across a roadway in which the present invention may be employed.

FIG. 2 illustrates a remote sensing device in which the present invention may be employed.

FIG. 3 illustrates one embodiment of the present invention wherein the center wavelength is shifted away from the characteristic wavelength of the component to be detected.

FIG. 4 illustrates a second embodiment of the present invention wherein the detection bandwidth is adjusted.

FIG. 5 illustrates a third embodiment of the present invention wherein the center wavelength is shifted away from the characteristic wavelength of the constituent to be detected and the detection bandwidth is adjusted.

DETAILED DESCRIPTION OF THE PREFERRED EMBODIMENTS

The present invention relates to an improvement in vehicle emission testing devices and methods for remote sensing of vehicle emissions. More specifically, the present invention provides a system and method for selecting radiation filters which permit a certain bandwidth of radiation to pass through to corresponding detectors, said bandwidth being selected to center about a center wavelength which is in the vicinity of the characteristic wavelength of the constituent to be detected and to exclude radiation of other wavelengths, especially wavelengths which may be absorbed by one or more contaminants. Contaminants such as pollutants, dust and water are some of the examples of undesirable substances which may be encountered when using RSD. By carefully selecting the bandwidth of one or more radiation filters employed in the RSD, this invention can substantially reduce or eliminate interference with the detection of a desired substance by the detection of one or more undesirable contaminants.

In order to effectively carry out the present invention, an initial determination must be made of the characteristic wavelengths of each constituent of the vehicle emission which is to be detected. This can be accomplished by subjecting known concentrations of each constituent to spectral analysis. In fact, the characteristic wavelengths of the most important constituents of standard gasoline fueled motor vehicle emissions, namely, hydrocarbons, carbon monoxide, carbon dioxide and nitrogen oxides ($NO_x$) are known from the literature.

Also important to the present invention is to determine the bandwidth about the characteristic wavelength within which the constituents absorb sufficient radiation to provide a measurable response. This bandwidth can be determined using the same technique of spectral analysis as for determining the characteristic wavelengths.

Secondly, a determination must be made of one or more of the contaminants which will typically be encountered by the radiation employed to measure the specific constituents of the vehicle emission. Once the contaminants are known, the characteristic wavelengths and the bandwidths about the characteristic wavelengths of each contaminant, within which the contaminant absorbs sufficient radiation to produce a measurable response, should also be determined, again using spectral analysis.

Using the foregoing information, a plot of the radiation absorption characteristics of the constituents to be detected and the contaminants as a function of wavelength can be made. Using this plot, center wavelengths and associated bandwidths centered about such center wavelengths can be selected for the detection and measurement of each constituent. More specifically, the center wavelength and bandwidth for detection of a particular constituent is selected in accordance with the present invention in order to reduce or eliminate overlap with wavelengths of radiation at which one or more contaminants produce a measurable response. In this manner, skewing of measurements of the desired constituents due to inadvertent detection of contaminants can be reduced or eliminated.

It is straightforward to select a center wavelength and bandwidth for detection of a constituent for which there is no overlap between the absorption spectrum of that constituent and the absorption spectrum of one or more contaminants. In such case, the center wavelength is preferably selected to be the characteristic wavelength of the constituent, ie., the wavelength, at which the highest level of radiation absorption is measured to thereby provide a strong detectable response characteristic of that constituent. The bandwidth is selected to provide a strong detectable response characteristic as well.

The present invention, however, is directed to the more difficult scenario wherein the absorption spectrum of one or more contaminants overlaps with the absorption spectrum of the desired constituent. In such a case, it may be undesirable to select the characteristic wavelength of the constituent as the center wavelength since a response may be elicited not only by the desired constituent, but also by one or more contaminants.

The present invention provides several potential solutions to this problem. First, the center wavelength for detection of a particular desired constituent may be selected such that it is shifted away from the characteristic wavelength for that constituent by a distance sufficient to eliminate or minimize overlap between the absorption spectrum of one or more contaminants and a detection bandwidth for that constituent which is centered about the selected center wavelength. Second, the detection bandwidth for a particular constituent can be narrowed to eliminate overlap between the absorption spectrum of one or more contaminants and the detection bandwidth for the desired constituent. Third, a combination of the shifting of the center wavelength and adjustment of the size of the bandwidth may be employed to accomplish the same goal.

Figure 3:
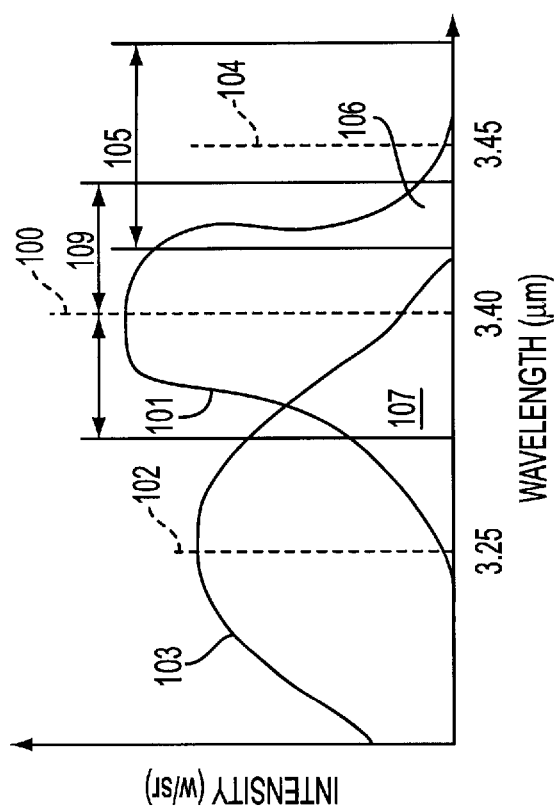

As shown in FIG. 3, in some instances it may be sufficient to shift the center wavelength for detection of a particular constituent away from the characteristic wavelength in order to eliminate interference from one or more contaminants. More particularly, the characteristic wavelength 100 of a particular constituent such as hydrocarbon, may be at about 3.40 $\mu$m. The hydrocarbon may, for example, exhibit an absorption spectrum 101 as shown in FIG. 3 centered about its characteristic wavelength of 3.40 $\mu$m. Water, a contaminant, may have a characteristic wavelength 102 at 3.25 $\mu$m and an absorption spectrum 103 centered about the characteristic wavelength 102 as shown in FIG. 3. If a detection bandwidth 109 centered about the characteristic wavelength 100 of hydrocarbon is selected, it can be seen that within such a detection bandwidth 109, there will also be a measurable response due to the contaminant water in the area of overlap 107. In order to eliminate this problem, a center wavelength 104 can be selected as 3.45 $\mu$m (i.e., shifted away from the characteristic wavelength) with a corresponding detection bandwidth 105 such that within the detection bandwidth 105, hydrocarbon produces a measurable response in the region 106 but, at the same time there is no substantially measurable response due to the contaminant water.

Figure 4:
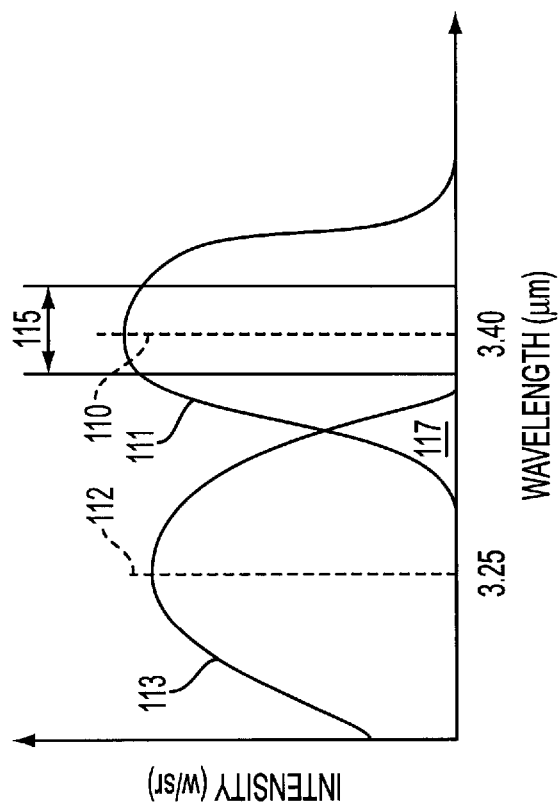

Another embodiment of the present invention is depicted in FIG. 4. In this embodiment, the characteristic wavelength 110 of the desired constituent hydrocarbon is again at 3.40 and the hydrocarbon has an absorption spectrum 111. In this embodiment, the contaminant water again has, for the purpose of this example, a characteristic wavelength of about 3.25, indicated at 112, but now exhibits an absorption spectrum 113 as shown in FIG. 4 which has less overlap 117 with the absorption spectrum 111 of the hydrocarbon than that shown in FIG. 3. In such case, interference from the contaminant water can be substantially eliminated by selection of a narrow detection bandwidth 115 which is still centered about the characteristic wavelength 110 of the hydrocarbon rather than by shifting the center wavelength of the detection bandwidth for hydrocarbon away from the characteristic wavelength as in the embodiment of FIG. 3.

Figure 5:
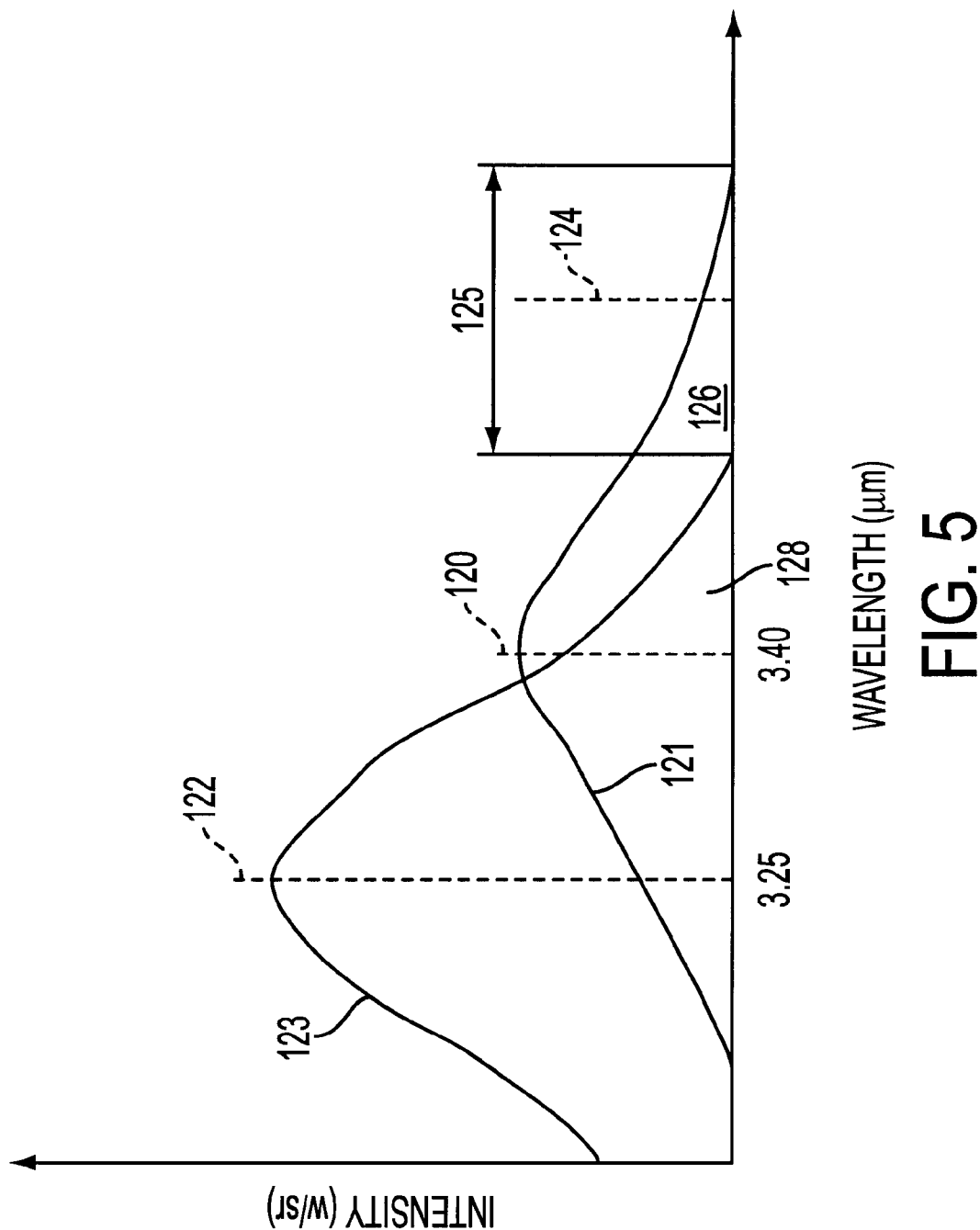

An example of a third embodiment of the present invention is depicted in FIG. 5. In this embodiment the desired constituent (e.g., hydrocarbon) again exhibits a characteristic wavelength 120 of 3.40 $\mu$m. However, the absorption spectrum 121 of the desired constituent is broader and flatter than that of the constituent illustrated in FIG. 3. The contaminant (e.g., water) again exhibits a characteristic wavelength 122 of 3.25 $\mu$m but has an absorption spectrum 123 which has a large overlap 128 with the absorption spectrum 121 of the desired constituent. In this example, the problem caused by the contaminant can be solved by shifting the center wavelength 124 away from the characteristic wavelength 120 of the desired constituent as shown in FIG. 5. However, due to the limited response to the desired constituent in the vicinity of the selected center wavelength 124, it is also desirable to select a wide detection bandwidth 125 since this will increase the measurable response 126 of the desired constituent as shown. This is an instance where both a shift of the center wavelength and a modification of the detection bandwidth are employed together to maximize the response of the desired constituent and minimize interference by one or more contaminants. Various other applications of these principles in any combination are within the scope of the invention.

The foregoing examples of the invention can be practiced by the selection of appropriate radiation filters for each application. Thus, once the desired center wavelength and detection bandwidth for a particular constituent is selected, an appropriate filter is employed to filter out substantially all radiation which has a wavelength outside the detection bandwidth and permit passage to a detector of radiation within the detection bandwidth. Radiation filters are conventional devices which can be fabricated to meet such specifications by persons skilled in the relevant technical field.

In one preferred embodiment of the present invention, a filter was selected to have a center wavelength of 3.45 $\mu$m for the purpose of detecting hydrocarbon. Standard hydrocarbon detectors employ filters having a center wavelength of 3.40 $\mu$m. It has been found that by shifting the center wavelength of the filter to 3.45 $\mu$m, a substantial reduction in the detector response due to the contaminant water was realized. This resulted in an improvement in the accuracy of the determination of the concentration of hydrocarbon by substantially eliminating the uncertainty which was previously caused by detection of the contaminant water within the detection bandwidth that was employed for detection of hydrocarbon.

The present invention can be incorporated into any RSD. For example, the present invention may be used in conjunction with the RSD taught in U.S. Pat. No. 5,210,702 ("'702 patent"), the disclosure of which is incorporated herein by reference to show the details of the components of the RSD.

One known compact, portable RSD in which the present invention may be employed is shown in FIG. 1 and comprises an infrared (IR) beam emitter 13, a detector 16 and a computer 17. In operation, the RSD measures the concentrations of at least hydrocarbon (HC), carbon monoxide (CO), and carbon dioxide ($CO_2$) within a vehicle's emission plume 29. The RSD determines the concentration by passing a beam of infrared radiation through the vehicle's exhaust as the vehicle 28 travels by the RSD positioned alongside the highway. The IR emitter 13 transmits a beam of IR energy along a path 15 which crosses the traffic lane 26 and encounters a detector 16. The IR emitter 13 is located on one side of the vehicle's path (such as a road or highway ramp) at a proper height so that the beam 15 intersects the vehicle's exhaust plume 29. Alternatively, an ultraviolet (UV) emitter 12 may be employed or a combination of an IR emitter 13 and a UV emitter 12 with a collimator 14 can be used. The IR emitter 13 sends the IR beam 15 into the detector 16 on a continuous basis. The detector 16 operate to convert the infrared energy to an electrical signal which is measured in voltage and is continuously transferred to the computer 17 where this information is used to compute and produce output signals indicative of the concentration of CO, $CO_2$, and HC in the vehicle's emission. Upon entry of a vehicle 28 into the optical path of the beam 15, a drop in the reference voltage signals the presence of the vehicle 28. Voltages from each of the signal channels (i.e., the CO, the $CO_2$, the HC, and the reference detectors 16 signals) that were acquired prior to the vehicle 28 interrupting the beam 15 are stored by the computer 17. While the vehicle 28 continues to block the beam, zero correction voltages for each channel are acquired. As the vehicle 28 exits the beam 15 so that the beam 15 is again received by the detector 16 (from about 0.1 to about 1 second) voltage versus time data streams from each of the channels are acquired by the computer 17. A data stream time train of from about 0.1 to about 1.0 second is a preferred selected time, chosen for convenience. The signals received are averaged over from about 1 millisecond to about 20 milliseconds, with about 10 milliseconds being preferred. By thus averaging the signal, a better signal to noise ratio is obtained. Emission results are obtained by computing the ratios of the CO, HC, and $CO_2$ voltages (I) to the reference voltages ($I_0$) and rescaling these arbitrary units into calibrated CO and $CO_2$ values with the use of calibration curves determined in a laboratory utilizing special flow cells with controlled mixture of CO, $CO_2$ and HC. Those data are then analyzed by the computer 17 by a least squares procedure to determine the concentration of each constituent within the exhaust emission.

A visual recording device, such as a video camera 20 of any desired make or manufacture is preferably positioned along the roadway 26 spaced from the detector 16 and oriented so as to focus on the area between the detector 16 and the radiation source 11. The camera 20 is directly linked to the computer 17 such that as a vehicle 28 interrupts the beam 15, the camera 20 is activated so as to record the end, preferably rear, of the vehicle 28 including the license plate thereof. A visual monitor 22 is linked to the computer 17 and the camera 20 so as to provide on-line visual identification of the vehicle 28 for remote location, while a video recording device 24 of any desired type is utilized to provide a permanent record of what is displayed on the monitor 22. While the display on the monitor 22 provides a picture of the rear of the vehicle 28, the computer 17, upon determining the CO, $CO_2$, and HC levels, displays that information on the monitor display simultaneously with the viewing the rear of the vehicle 28 so that the information is overlaid onto the picture of the vehicle 28. In addition, the video image of the vehicle is further overlaid by the date and time of the emissions recording so as to provide a permanent record for the particular vehicle 28. Furthermore, the computer 17 may have on-line access to the Department of Motor Vehicle Registrations so that it can also further provide the video display with the make, model, and year of the vehicle 28 based on the license plate information recorded so as to provide real-time determination as to emissions compliance or non-compliance with any state regulations of a particular make, model, and year vehicle.

As can be seen from the above, the present invention provides a unique system for the remote measuring and monitoring of emissions from moving motor vehicles. In particular, the present invention provides a method and apparatus to shift the detection bandwidth and/or center wavelength of a filter to minimize the detection of a contaminant. This particular invention allows a remote sensing and measuring so that vehicles do not have to be stopped and can be spot-checked at any given time. Moreover, this particular system permits the visual display as well as permanent recording of such display of the actual vehicle, including license plate identification which is displayed in conjunction with the exhaust measurements. Such a system could be utilized to enforce complete emission standards under real use conditions and/or to simply obtain real-time measurements so as to permit vehicle owners to be made aware of necessary corrections of vehicle emissions.

Figure 2:
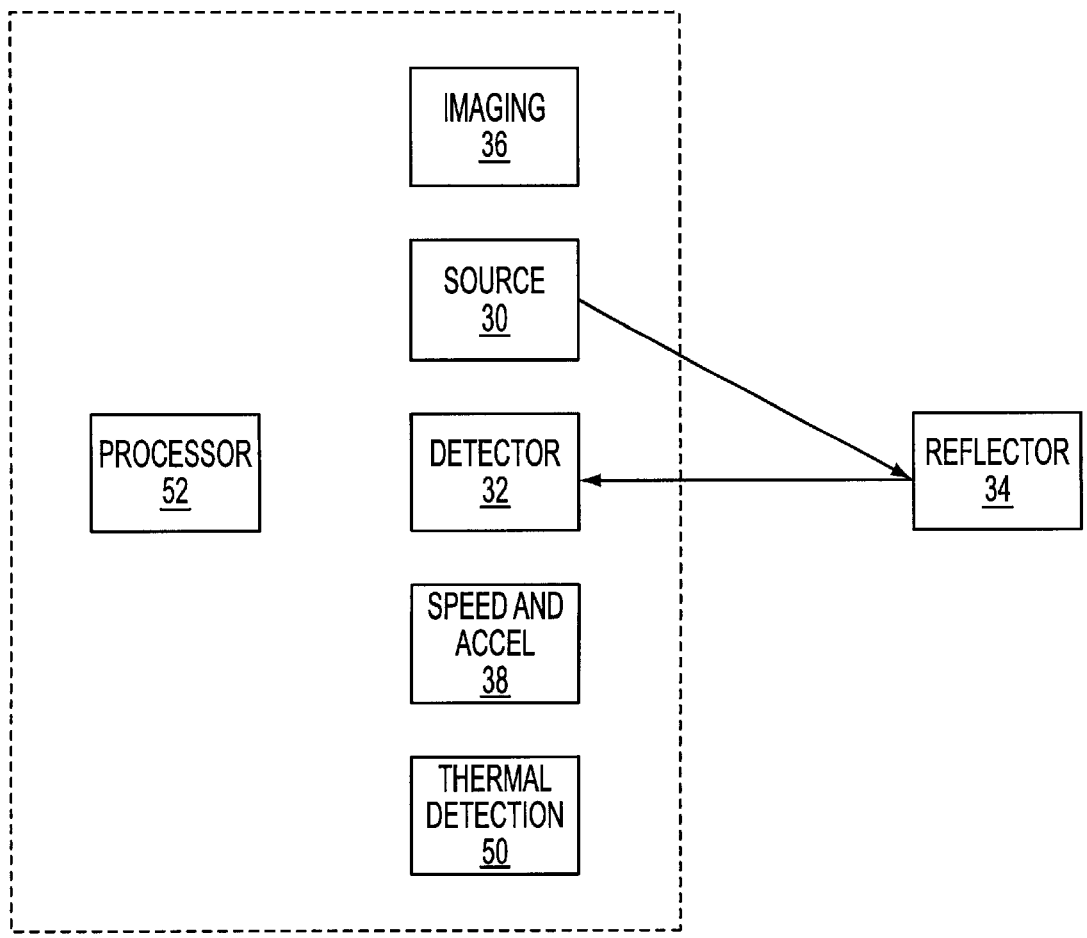

FIG. 2 shows a schematic representation of various components of the remote sensing detector (RSD) unit. Embodiments of the invention may include some or all of the various components as described below.

Radiation Source

Preferably, an RSD unit comprises a source of electromagnetic radiation 30 which may be used in the absorption spectroscopy measurement of the vehicle exhaust emissions. Preferably, source 30 may comprise an infrared (IR) radiation source. Some embodiments of the RSD unit may include other types of radiation sources, for example, an ultraviolet (UV) source, a visible radiation source, or a combination of sources.

Some embodiments may use ambient radiation as a source. For example, IR radiation from a concrete or asphalt road heated by sunradiation may be used as a radiation source for emission measurements. These embodiments may be characterized as passive or "sourceless" systems in contrast with sources that actively emit radiation.

Radiation Detector

The RSD unit may further comprise a plurality of detectors 32 of electromagnetic radiation. The detectors 32 are preferably chosen to permit detection of electromagnetic radiation emitted by the source. For example, the detectors 32 may comprise a photodetector (e.g., a photodiode), a photomultiplier tube (PMT), a spectrometer or other suitable radiation detector. For embodiments using ambient radiation sources an appropriately sensitive detector may be used. For example, a mercury cadmium telluride (Hg Cd Te) photodetector may be used to detect ambient IR radiation. Other detectors are possible.

Reflector

Preferably, the RSD unit may comprise a reflector 34 mounted in a manner to allow radiation from the source 30 to be reflected into the detector 32 for analysis. The reflector 34 may comprise a mirror, prism, diffraction grating, beam splitter or other device suitable for directing the radiation of the source 30. In one embodiment the reflector 34 may comprise a lateral transfer mirror assembly used to reflect the source 30 radiation back along a path displaced laterally (or vertically, if so oriented) from the incident direction.

Alternative embodiments of the RSD unit may be arranged to operate without a reflector 34. For example, source 30 may be oriented to emit radiation directly into detector 32. Such an embodiment may comprise source 30 and detector 32 located on opposite sides of a roadway.

Imaging Unit

The RSD unit may also include an imaging unit 36 which may be used to capture or record an image of a vehicle passing through the detection system. The imaging unit 36 may be arranged to record an image of a vehicle at a specified location in the detection system. The imaging unit 36 may comprise, for example, a camera, such as a film, video or digital camera. Other imaging devices may also be used.

Preferably, the imaging unit 36 may record an image of the vehicle identification tag (i.e., license plate). Tag information may be processed, using a suitable data processor, to identify additional information about the respective vehicle. For example, Motor Vehicle Department databases may be accessed to retrieve vehicle owner information, vehicle make, model type, model year and other information. In some embodiments, this additional information may be incorporated into the emission sensing data analysis. For example, the make and model year of the vehicle may be used to input information (e.g., whether the vehicle includes a carburetor or fuel injector, etc.) into certain data processing routines.

Speed and Acceleration

The RSD unit may also include a speed and acceleration detection unit 38. Preferably, a vehicle's speed (and, therefore, acceleration) through the detection system may be measured using speed detection unit 38. For example, the speed detection unit may comprise an arrangement of laser beams, detectors and associated timing circuitry. The arrangement of laser beams may be arranged to traverse the path of a vehicle at various points in the detection system. As a vehicle passes through the detection system it will cause interruptions in the laser beams. The times at which the beam interrupts occur may be used to calculate the vehicle's speed and acceleration. Other methods of detecting vehicle speed and acceleration may also be used. For example, radar systems may be used to determine vehicle speed and acceleration.

Alternatively, transducers, piezoelectric elements or other "drive over" detectors may be placed at locations in the roadway to monitor vehicle passage through the system. Preferably, the speed and acceleration data may be input into a data processing unit 52 to accurately characterize vehicle operation conditions (e.g., accelerating or decelerating). Other uses of the speed and acceleration data are also possible.

Thermal Detection Unit

Some embodiments of the invention may incorporate a thermal detection unit 50. Preferably, the thermal detection unit 50 may comprise a non-contact thermometer system. For example, an IR thermometer may be used to optically detect the temperature of remote objects. Other temperature detection systems may also be used.

Preferably, the thermal detection unit is used to detect the temperature of portions of the vehicle passing through the RSD system. Some embodiments may use direct sensing of the area of interest. For example, an IR thermometer may be aimed at the underside of a passing vehicle to detect the temperature(s) of vehicle components (e.g., engine, catalytic converter, muffler, etc.). Indirect sensing may also be used. For example, an IR thermometer may be aimed at the roadway to measure the heat reflected from the underside of a vehicle.

Preferably, the thermal information recorded by the thermal imaging unit 50 may be incorporated into the processing for the vehicle emission data. For example, a temperature reading of a vehicle's engine may indicate that the engine has just recently been started (i.e., the engine is "cold" or has not reached normal operating temperature). Such a cold engine reading may initiate alternative data processing for the emission data.

Thermal detection unit 50 data may also be used for other data handling procedures. For example, it may be preferable to identify whether a vehicle's catalytic converter is operational. A temperature reading indicating that the catalytic converter is "cold" may indicate that the converter is not functioning. However, a cold catalytic converter might also indicate that the vehicle has only been driven for a short period and, thus, has not achieved operational temperature. Embodiments of the present invention reduce the chance of such a potentially misleading reading by detecting the temperature of other portions of the vehicle. For example, a temperature reading indicating that the catalytic converter is cold, but the brake rotor (or engine) is "hot" indicate, with greater certainty, that the vehicle has reached operating temperature and the catalytic converter is indeed non-operational. Other uses for collected thermal data are also possible.

Processing Unit

The RSD unit preferably includes a data processing unit 52 to, among other things, carry out analysis of detected data. The processing may be accomplished using a suitable processing device, for example, a computer or other microprocessor. The processing unit 52 may include software to accomplish desired analysis of collected data For example, the software may be used to calculate the concentrations of various exhaust gas constituents (e.g., HC, $CO_2$, $NO_x$, CO, etc.), the decay rate (e.g., dissipation in time) of the exhaust constituents, the opacity of the exhaust plume, the temperature, speed and acceleration of the vehicle, and other calculations.

The processing unit may also comprise software or routines to accomplish other data analysis functions. For example, the vehicle emission data may be checked for running losses. Running losses may typically include emission readings due to fuel system leaks on a vehicle (e.g., leaky fuel tank filler cap, fuel line, etc.), blow by emissions (ie., emissions due to other vehicles in the vicinity) or other systematic losses.

The data processing may also include software or routines to accomplish various vehicle owner notification processes. For example, a vehicle that has been recorded as "clean" (i.e., in compliance with certain predetermined emission levels) may, upon a second recording of "clean," receive notification of the fact. Coordination with local authorities may be arranged to grant vehicle owners a waiver or pass of local emission certification procedures upon receiving such clean notification. Likewise, vehicles that fail to meet predetermined emission levels may receive notification requiring the owner to remedy the non-compliance. Other data processing functions are possible.

Other embodiments and uses of the invention will be apparent to those skilled in the art from consideration of the specification and practice of the invention disclosed herein. The specification and examples should be considered exemplary only. The scope of the invention is only limited by the claims appended hereto.

What is claimed is:

1. A method for selecting a detection bandwidth centered about a center wavelength for at least one constituent of a vehicle emission, said method comprising the steps of:

(a) determining a constituent characteristic wavelength of at least one constituent of the vehicle's emission to be detected;

(b) determining a bandwidth about the constituent characteristic wavelength within which said at least one constituent absorbs radiation;

(c) determining one or more contaminants which may be encountered by radiation employed to detect said at least one constituent in a vehicle emission plume;

(d) determining a contaminant characteristic wavelength of said at least one contaminant;

(e) determining a bandwidth about the contaminant characteristic wavelength of said at least one contaminant within which said at least one contaminant absorbs radiation;

(f) comparing the constituent characteristic wavelength and the contaminant characteristic wavelength and the bandwidth about the constituent characteristic wavelength of said at least one constituent and the bandwidth about the contaminant characteristic wavelength of said at least one contaminant; and (g) selecting a detection bandwidth based on said comparison in step (f) by shifting the center wavelength of the detection bandwidth away from the constituent characteristic wavelength and adjusting the size of the detection bandwidth.

2. A method according to claim 1, wherein the constituent to be detected is selected from the group consisting of hydrocarbon, carbon monoxide, carbon dioxide, and nitrogen oxides.

3. A method according to claim 1, the step (g) further comprises the step of shifting the center wavelength of the detection bandwidth away from the contaminant characteristic wavelength.

4. A method according to claim 1, the step (g) further comprises the step of adjusting the size of the detection bandwidth.

5. A method for selecting a radiation filter for detection of at least one constituent of a vehicle emission, said method comprising the steps of:
- (a) determining a constituent characteristic wavelength of at least one constituent of the vehicle's emission to be detected;
- (b) determining a bandwidth about the constituent characteristic wavelength within which said at least one constituent absorbs radiation;
- (c) determining one or more contaminants which may be encountered by radiation employed to detect said at least one constituent in a vehicle emission plume;
- (d) determining a contaminant characteristic wavelength of said at least one contaminant;
- (e) determining a bandwidth about the contaminant characteristic wavelength of said at least one contaminant within which said at least one contaminant absorbs radiation;
- (f) comparing the constituent characteristic wavelength and the contaminant characteristic wavelength and the bandwidth about the constituent characteristic wavelength of said at least one constituent and the bandwidth about the contaminant characteristic wavelength of said at least one contaminant;
- (g) selecting a detection bandwidth based on said comparison in step (f) by shifting the center wavelength of the detection bandwidth away from the constituent characteristic wavelength and adjusting the size of the detection bandwidth; and
- (h) selecting a radiation filter which permits passage of radiation within the detection bandwidth and filters out substantially all other radiation.

6. A method according to claim 5, wherein the constituent to be detected is selected from the group consisting of hydrocarbon, carbon monoxide, carbon dioxide, and nitrogen oxides.

7. A method according to claim 5, the step (g) further comprises the step of shifting the center wavelength of the detection bandwidth away from the contaminant characteristic wavelength.

8. A method according to claim 5, the step (g) further comprises the step of adjusting the size of the detection bandwidth.

9. A method for detecting one or more constituents of a vehicle exhaust emission, said method comprising the steps of:
- (a) emitting radiation from a radiation source;
- (b) passing said radiation through a vehicle exhaust emission;
- (c) filtering said radiation which passed through said vehicle's exhaust emission with a radiation filter which is selected to permit a bandwidth centered about a center wavelength of 3.45 $\mu$m to pass through to a detector, said bandwidth being selected such that the center wavelength is a characteristic wavelength of a hydrocarbon to be detected and there is substantially no absorption of radiation within said selected bandwidth by one or more contaminants which may be encountered by said radiation;
- (d) detecting said filtered radiation;
- (e) determining the concentration of the the hydrocarbon within the vehicle's exhaust emission.

* * * * *